United States Patent [19]

Tsuchiya

[11] Patent Number: 5,694,931
[45] Date of Patent: Dec. 9, 1997

[54] METHOD AND APPARATUS FOR MEASURING CONCENTRATION OF ABSORPTIVE CONSTITUENT IN SCATTERING MEDIUM

[75] Inventor: Yutaka Tsuchiya, Hamamatsu, Japan

[73] Assignee: Hamamatsu Photonics K.K., Hamamatsu, Japan

[21] Appl. No.: 531,771

[22] Filed: Sep. 21, 1995

[30] Foreign Application Priority Data

Sep. 22, 1994 [JP] Japan .................. 6-228253

[51] Int. Cl.$^6$ .................................................. A61B 5/00
[52] U.S. Cl. .................. 128/633; 128/664; 128/665
[58] Field of Search ................... 128/633, 664, 128/665

[56] References Cited

U.S. PATENT DOCUMENTS

| | | | |
|---|---|---|---|
| 5,139,025 | 8/1992 | Lewis et al. | 128/665 |
| 5,386,827 | 2/1995 | Chance et al. | 128/633 |
| 5,413,098 | 5/1995 | Benaron | 128/633 |

FOREIGN PATENT DOCUMENTS 4-191642  7/1992  Japan .

OTHER PUBLICATIONS

Wilson et al, "Optical Reflectance and Transmittance of Tissues: Principles and Applications", IEEE Journal Of Quantum Electronics, vol. 25, No. 12, Dec. 1990, pp. 2186–2199.

Wilson et al, "Time–Dependent Optical Spectroscopy and Imaging for Biomedical Applications", Proceedings Of The IEEE, vol. 80, No. 6, Jun. 1992, pp. 918–930.

Patterson et al, "Time Resolved Reflectance and Transmittance for the Non–Invasive Measurement of Tissue Optical Properties", Applied Optics, vol. 28, No. 12, Jun. 15, 1989, pp. 2331–2336.

Jacques, "Time–Resolved Reflectance Spectroscopy in Turbid Tissues", IEEE Transactions On Biomedical Engineering, vol. 36, No. 12, Dec. 1989, pp. 1155–1161.

Sevick et al, "Quantitation of Time– and Frequency-Resolved Optical Spectra for the Determination of Tissue Oxygenation", Analytical Biochemistry 195, pp. 330–351.

Arridge et al, "The Theoretical Basis for the Determination of Optical Pathlengths in Tissue: Temporal and Frequency Analysis", Phys. Med. Biol, 1992, vol. 37, No. 7, pages.

Schmitt et al, "Interference of Diffusive Light Waves", J. Opt. Soc. Am. A, vol. 9, No. 10, Oct. 1992, pp. 1832–1843.

Pogue et al, "Frequency–Domain Optical Absorption Spectroscopy of Finite Tissue Volumes Using Diffusion Theory", Phys. Med. Biol 39 (1994), pp. 1157–1180.

Oda et al, "Quantitation of Absolute Concentration Change in Scattering Media By the Time–Resolved Microscopic Beer–Lambert Law", Oxygen Transport to Tissue XV, Plenum.

Primary Examiner—Lee S. Cohen
Assistant Examiner—Eric F. Winakur
Attorney, Agent, or Firm—Cushman Darby & Cushman IP Group of Pillsbury Madison & Sutro, LLP

[57] ABSTRACT

A method for measuring a concentration of an absorptive constituent in a scattering medium comprises the steps of emitting of light having two or more predetermined wavelengths; making said light incident at a light incidence position into said scattering medium; detecting said light at one or more photodetection points to acquire one or more photodetection signals; detecting light quantities and average flight pathlengths for said respective wavelengths of light based on said signals; and obtaining a concentration of said absorptive constituent by arithmetic processing using said light quantities and average flight pathlengths based on a predetermined relationship. The method permits absolute-value measurement of the concentration of the absorptive constituent inside the scattering medium having various exterior shapes.

16 Claims, 11 Drawing Sheets

STRUCTURE OF APPARATUS OF THE FIRST EMBODIMENT

EXAMPLE OF TIME - RESOLVED RE-EMISSION

NEAR-INFRARED ABSORPTION SPECTRA OF Hb (0.37mM) AND Mb (0.15mM)

NEAR-INFRARED ABSORPTION SPECTRA OF Hb (0.37mM) AND Mb (0.15mM)

STRUCTURE OF APPARATUS OF THE
FIRST EMBODIMENT

CONDENSER LENS

OPTICAL FIBER

PINHOLE

LIGHT INCIDENCE FROM THE
INSIDE OF SCATTERING MEDIUM

DIRECT DETECTION

OPTICAL FIBER

LENS COUPLING

STRUCTURE OF APPARATUS OF THE SECOND EMBODIMENT

CONFIGURATION OF A LIGHT INCIDENCE POSITION AND PHOTODETECTION POINTS OF THE APPARATUS OF THE SECOND EMBODIMENT

STRUCTURE OF APPARATUS OF THE THIRD EMBODIMENT

METHOD FOR GENERATING MODULATED
LIGHT WITH A LASER DIODE

METHOD FOR GENERATING MODULATED
LIGHT UTILIZING BEATS
(USING TWO CW LASERS)

METHOD FOR GENERATING MODULATED
LIGHT WITH AN OPTICAL MODULATOR

METHOD AND APPARATUS FOR MEASURING CONCENTRATION OF ABSORPTIVE CONSTITUENT IN SCATTERING MEDIUM

BACKGROUND OF THE INVENTION

1. Field of the Invention

The present invention relates to a method and apparatus for measuring the absolute concentration of absorptive constituent in a scattering medium, which is so arranged that light having two or more predetermined wavelengths, at which the scattering coefficients are equal or regarded as equal, are made incident into the scattering medium such as a living tissue, which could take a variety of exterior shapes, and that the light of the predetermined wavelengths is detected after diffusively having propagated through inside the scattering medium and when escaping from the surface thereof, to obtain quantities of light and average flight pathlengths (average optical pathlengths) at one or more positions of detection, whereby the concentration of a specific absorptive constituent inside the scattering medium or the absolute amount thereof, an oxygen saturation of hemoglobin, and further, a time change or spatial distribution thereof can be measured at high accuracy and in a non-invasive fashion without being affected by the exterior shape of the scattering medium.

2. Related Background Art

There are very high demands for non-invasive and precise measurement of the concentration of a specific absorptive constituent inside the scattering medium such as a living tissue or the absolute amount thereof, and a time change or spatial distribution thereof in addition, and a variety of methods and attempts have been made to meet the demands, for example methods using continuous light (CW light) or modulated light (for example, pulsed light, square-wave light, sinusoidally modulated light, etc.), methods utilizing light beams with different wavelengths, etc.

These conventional techniques, however, have not developed a satisfactory method or apparatus for accurately measuring the concentration of a specific absorptive constituent in various media which could take a variety of shapes, such as a living tissue, or a particular tissue which usually has individual differences in shape. This has been a serious problem in non-invasive measurement of living samples utilizing the light, and improvement has strongly been desired.

The light incident into the scattering medium such as a living tissue diffusively propagates inside the medium while scattered and absorbed, and then part thereof comes out of the surface of the medium. Since the outside of the scattering medium is normally filled with air, the light escaping from the surface dispersively propagates in a free space.

For measuring information on the inside of the scattering medium, the light escaping from the surface is detected as described above. With scattering media in different shapes, for example depending upon sphere or rectangular parallelepiped, a great difference will appear in quantity or behavior of the light escaping from a predetermined position of the surface therefrom.

Therefore, in order to improve the accuracy of such measurement, it is necessary to understand the behavior of the light inside the scattering medium. It is recently known that the behavior of the light inside the scattering medium can be analyzed, experimented, or investigated by the Monte Carlo calculation (Monte Carlo simulation) using a computer, or can be described or analyzed accurately to some extent by the photon diffusion theory.

As described above, the Monte Carlo simulation and photon diffusion theory have been used heretofore in order to understand the behavior of the light inside the scattering medium.

SUMMARY OF THE INVENTION

The inventor found out that the above conventional methods included the following problems.

Namely, the Monte Carlo simulation requires a very long time for calculation and does not permit us to calculate the concentration etc. of the specific absorptive constituent inside the scattering medium from the result.

In utilizing the photon diffusion theory, it is necessary to set boundary conditions in order to actually solve photon diffusion equations. However, the boundary conditions are greatly dependent on the exterior shape of scattering medium; thus, for accurate measurement, new boundary conditions must be set for each of scattering media with different shapes to solve photon diffusion equations therefor. Further, shapes of scattering media for which the boundary conditions can be set accurately to some extent are limited to extremely simple ones, such as an infinite space, a semi-infinite space, an infinite circular cylinder, an infinitely spreading slab with a finite thickness, and so on. Consequently, approximate boundary conditions have to be used for measurement of an object of a complex shape, such as a living tissue, which causes a great measurement error.

As described above, the conventional technology has failed to develop a method for handling diffusing light, which was capable of being systematically applied to scattering media of different shapes, and therefore, it is impossible to accurately measure concentrations etc. of a specific absorptive constituent inside the scattering media having different shapes by systematically applying the conventional techniques.

SUMMARY OF THE INVENTION

Solving the above problems, an object of the present invention is to provide a method and apparatus for measuring a concentration of an absorptive constituent inside a scattering medium, which newly discloses basic relationships associated with the behavior of the light inside the scattering media of different shapes, which realizes measurement of concentrations or absolute amounts of a specific absorptive constituent inside the scattering media having various shapes, etc., utilizing the relationships, which greatly improves the accuracy of the measurement, and which can measure a time change or spatial distribution of those.

The present invention involves such a technique that light having two or more predetermined wavelengths, at which the scattering coefficients are equal or regarded as equal, are made incident into a scattering medium, which could take various exterior shapes, light quantities and average flight pathlengths are obtained at a position of photodetection for the light of the predetermined wavelengths, and from these values, a concentration or an absolute amount of a specific absorptive constituent is obtained by arithmetic processing without being affected by the shape of scattering medium.

The present invention provides a method for measuring a concentration of an absorptive constituent in a scattering medium, comprising:

(a) a step of emitting light having two or more predetermined wavelengths, at which the scattering coefficients are equal or regarded as equal, toward a scattering medium which is a measured object;

(b) a step of making the light incident into the scattering medium at a light incidence position and making the light propagate through the scattering medium;

(c) a step of detecting the light having propagated through the scattering medium, at one or more photodetection points different from the light incidence position to obtain one or more photodetection signals;

(d) a step of detecting light quantities and average flight pathlengths at the one or more photodetection points for the respective wavelength light, based on the one or more photodetection signals; and (e) a step of obtaining a concentration of the absorptive constituent by arithmetic processing using the light quantities and the average flight pathlengths, based on a predetermined relationship as to the light quantities, the average flight pathlengths, and a difference between absorption coefficients per unit concentration of the absorptive constituent for the respective wavelength light.

The light having two or more predetermined wavelengths may be pulsed light having two or more predetermined wavelengths.

The light having two or more predetermined wavelengths may include two or more components of sinusoidally modulated light having a predetermined modulation frequency component, the light quantities may be calculated from (i) dc components of the photodetection signals or (ii) amplitudes of the predetermined modulation frequency component (signal) included in the photodetection signals, and the average flight pathlengths may be calculated from phase delays (phase differences) of the predetermined modulation frequency component (signal) included in the photodetection signals.

Further, light having two or more predetermined wavelengths may include two or more modulated light components, each having a predetermined repetitive modulation frequency component, the light quantities may be calculated from (i) dc components of the photodetection signals or (ii) amplitudes of the predetermined repetitive modulation frequency component (signal) or a frequency component (signal) of an integral multiple thereof, included in the photodetection signals, and the average flight pathlengths may be calculated from phase delays (phase differences) of the predetermined repetitive modulation frequency component (signal) or a frequency component (signal) of an integral multiple thereof, included in the photodetection signals.

The predetermined relationship among the light quantities, the average flight pathlengths, and the difference between the absorption coefficients per unit concentration of the absorptive constituent for the respective kinds of light having the wavelengths is preferably a relationship derived from such a relation that a partial differentiation of a natural logarithm of a light quantity detected with respect to an absorption coefficient is equal to an average flight pathlength.

In one embodiment of the method of the present invention, the above step (e) comprises obtaining the concentration of the absorptive constituent in the scattering medium by arithmetic processing using the light quantities and the average flight pathlengths, based on the relationship expressed by the following formula:

$$V = (\epsilon_2 - \epsilon_1)^{-1} \times$$
$$[p\langle L_1(\lambda_1)\rangle + (1-p)\langle L_1(\lambda_2)\rangle]^{-1} \times$$
$$\ln[I_1(\lambda_1)/I_1(\lambda_2)]$$

where

V: the concentration of the absorptive constituent, $\epsilon_1$: the absorption coefficient per unit concentration of the absorptive constituent for the light of the wavelength $\lambda_1$, $\epsilon_2$: the absorption coefficient per unit concentration of the absorptive constituent for the light of the wavelength $\lambda_2$, $\langle L_1(\lambda_1)\rangle$: the average flight pathlength of the incident light of the wavelength $\lambda_1$ at a photodetection point $r_1$, $\langle L_1(\lambda_2)\rangle$: the average flight pathlength of the incident light of the wavelength $\lambda_2$ at the photodetection point $r_1$, $I_1(\lambda_1)$: the (normalized) quantity of detected light for the incident light of the wavelength $\lambda_1$ at the photodetection point $r_1$, $I_1(\lambda_2)$: the (normalized) quantity of detected light for the incident light of the wavelength $\lambda_2$ at the photodetection point $r_1$, and p: a predetermined value, to satisfy the condition of $0 \leq p \leq 1$.

In another embodiment of the method of the present invention, the above step (e) comprises obtaining the concentration of the absorptive constituent in the scattering medium by arithmetic processing using the light quantities and the average flight pathlengths, based on a relationship expressed by the following formula:

$$V = (\epsilon_2 - \epsilon_1)^{-1} \times$$
$$[p\langle L_1(\lambda_1)\rangle + (1-p)\langle L_1(\lambda_2)\rangle -$$
$$q\langle L_2(\lambda_1)\rangle - (1-q)\langle L_2(\lambda_2)\rangle]^{-1} \times$$
$$\ln\{[I_1(\lambda_1) \cdot I_2(\lambda_2)]/[I_1(\lambda_2) \cdot I_2(\lambda_1)]\}$$

where

V: the concentration of the absorptive constituent, $\epsilon_1$: the absorption coefficient per unit concentration of the absorptive constituent for the light of the wavelength $\lambda_1$, $\epsilon_2$: the absorption coefficient per unit concentration of the absorptive constituent for the light of the wavelength $\lambda_2$, $\langle L_1(\lambda_1)\rangle$: the average flight pathlength at a photodetection point $r_1$, of the incident light of the wavelength $\lambda_1$, $\langle L_1(\lambda_2)\rangle$: the average flight pathlength at the photodetection point $r_1$, of the incident light of the wavelength $\lambda_2$, $\langle L_2(\lambda_1)\rangle$: the average flight pathlength at a photodetection point $r_2$, of the incident light of the wavelength $\lambda_1$, $\langle L_2(\lambda_2)\rangle$: the average flight pathlength at the photodetection point $r_2$, of the incident light of the wavelength $\lambda_2$, $I_1(\lambda_1)$: the quantity of detected light at the photodetection point $r_1$, for the incident light of the intensity $B_1$ and the wavelength $\lambda_1$, $I_1(\lambda_2)$: the quantity of detected light at the photodetection point $r_1$, for the incident light of the intensity $B_2$ and the wavelength $\lambda_2$, $I_2(\lambda_1)$: the quantity of detected light at the photodetection point $r_2$, for the incident light of the intensity $B_1$ and the wavelength $\lambda_1$, $I_2(\lambda_2)$: the quantity of detected light at the photodetection point $r_2$, for the incident light of the intensity $B_2$ and the wavelength $\lambda_2$, p: a predetermined value to satisfy the condition of $0 \leq p \leq 1$, and q: a predetermined value to satisfy the condition of $0 \leq q \leq 1$.

The present invention also provides an apparatus for measuring a concentration of an absorptive constituent in a scattering medium, comprising:

(a) a light source for emitting light having two or more predetermined wavelengths, at which the scattering coefficients are equal or regarded as equal, toward a scattering medium which is a measured object;

(b) light incidence means for making the light incident at a light incidence position into the scattering medium and then making the light propagate through the scattering medium;

(c) light detecting means (photodetection means) for detecting the light having propagated through the scattering medium, at one or more photodetection points different from the light incidence position to obtain one or more photodetection signals;

(d) parameter detecting means for detecting light quantities and average flight pathlengths at the one or more photodetection points for the respective wavelength light, based on the one or more photodetection signals; and (e) arithmetic processing means for obtaining a concentration of the absorptive constituent by arithmetic processing using the light quantities and the average flight pathlengths, based on a predetermined relationship among the light quantities, the average flight pathlengths, and a difference between absorption coefficients per unit concentration of the absorptive constituent for the respective wavelength light.

Here, the arithmetic processing means (e) is preferably arranged to obtain the concentration of the absorptive constituent, based on the predetermined relationship among the light quantities, the average flight pathlengths, and the difference between the absorption coefficients per unit concentration of the absorptive constituent for the respective wavelength light, which is derived from such a relation that a partial differential of a natural logarithm of the quantity of detected light with respect to the absorption coefficient is equal to the average flight pathlength.

Since the present invention involves arithmetic processing of the concentration of the specific absorptive constituent, based on the basic relationship holding for various scattering media of different shapes, that is, based on the relationship among the light quantities and the average flight pathlengths at a detection point, and the difference between absorption coefficients per unit concentration of the absorptive constituent for the light having two or more predetermined wavelengths, the concentration of the specific absorptive constituent can be accurately measured without being affected by the exterior shape of scattering medium. Also, the invention allows a time change or spatial distribution of the concentration of the specific absorptive constituent to be measured.

The present invention uses the light quantities and average flight pathlengths obtained from actually measured values, as parameters for the arithmetic processing of the concentration of the specific absorptive constituent. Since these parameters are those obtainable by utilizing almost all light gathered at the photodetection point, that is, those obtained in the integral form, high signal-to-noise ratios can be achieved, thereby achieving high measurement accuracy as a result.

In the present invention, the light having two or more predetermined wavelengths, at which the scattering coefficients are equal or regarded as equal, are let to be incident into the scattering medium, measurement is carried out for the light, the difference between the absorption coefficients of the absorptive constituent at the predetermined wavelengths is calculated from measured values, and the concentration of the specific absorptive constituent is obtained therefrom. On this occasion, if light signals are detected at two or more detection points, a difference between light quantities of incident light beams of different wavelengths can be eliminated, which permits more practical measurement with high accuracy.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The principle of the present invention is first explained prior to the description of the embodiments of the present invention.

Principle of the Invention

Let us consider a uniform scattering medium and suppose that light from a light source disposed on a surface of the scattering medium propagates inside the scattering medium and that a photodetector disposed on the surface detects light escaping therefrom. In this case, the exterior shape of the scattering medium is arbitrary as long as it is comprised of faces which can prevent diffusing light from being again incident thereinto.

Figure 1:
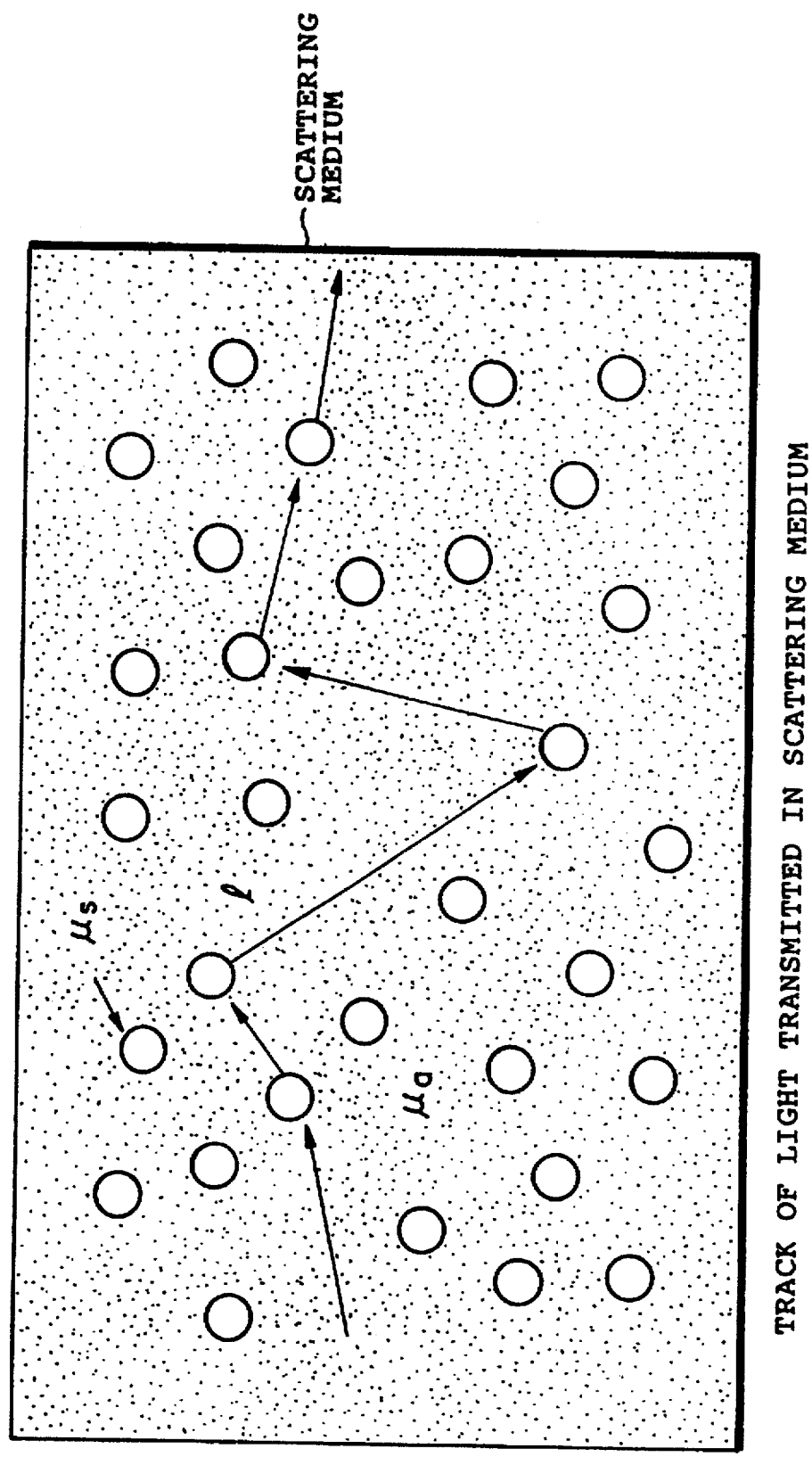
FIG. 1 is an explanatory drawing of a track of light having propagated through the inside of a scattering medium.

FIG. 1 shows an example of a track of detected light (or a photon) propagating inside a scattering medium.

The light is scattered by scattering particles, so that the optical path thereof is bent in a zigzag manner. Then, the Lambert-Beer law holds for the zigzag flight pathlength $l$, and the intensity of the propagating light exponentially attenuates against the zigzag flight pathlength (cumulative distance) $l$. On this occasion, the flight pathlength is given as $l=ct$, where c is a speed of the light in the medium and t is a time-of-flight.

Figure 2:
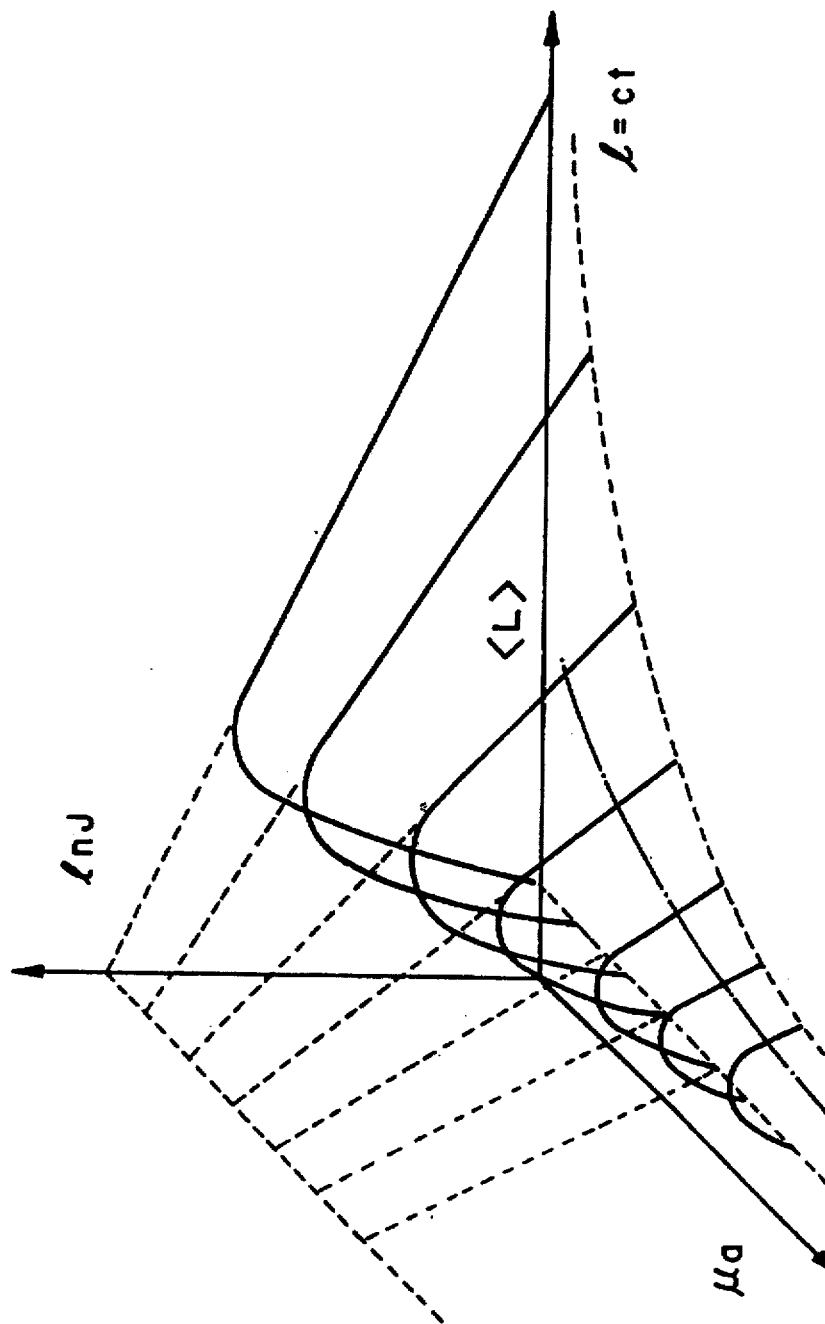
FIG. 2 is an explanatory drawing to show an example of time-resolved re-emission measured.

Furthermore, considering a time-resolved re-emission (waveform) $J(ct)$ of a photodetection signal obtained by time-resolved measurement, the flight pathlength $l$ corresponds to the abscissa, $ct=l$, of the time-resolved re-emission (waveform) $J(ct)$ of the photodetection signal, as shown in FIG. 2.

From the above, the following important relationships are obtained as to the flight pathlength and absorption of the zigzag light detected at time t, from which it is understood that the degree of absorption is associated with only the flight pathlength $l$ and absorption coefficient $\mu_a$.

$$ct = l = nl_s = n/\mu_s \quad (1)$$

$$\begin{aligned} J(ct) &= B_0 A(\mu_s', t)[\exp(-\mu_a/\mu_s)]^n \quad (2)\\ &= B_0 A(\mu_s', t)\exp(-\mu_a l)\\ &= B_0 A(\mu_s', t)\exp(-\mu_a ct) \end{aligned}$$

In the relationships, $l_s$: the mean free pathlength, where $l_s=1/\mu_s$, n: the number of collisions with scattering particles, $\mu_a$: the absorption coefficient, $\mu_s$: the scattering coefficient, $\mu_s'$: the transport scattering coefficient by similarity principle, $\mu_s'=(1-g)\mu_s$, where g is the mean cosine of the scattering angle, $B_0$: the intensity of light incident into the scattering medium, $B_0 A(\mu_s', t)$: a photodetection signal without absorption, that is, when $\mu_a=0$. Here, $l>>l_s$, and $A(\mu_s', t)$ represents the effect of scattering.

Next derived are the basic relationships as to the behavior of the light inside the scattering medium from the above relationship. Consider a single photon to be incident at $t=0$ on a medium and $J(\mu_s', \mu_a, t)$ to be the probability density function for escape at a given time t for a single photon. First, for the time-resolved re-emission, which is an ensemble of photons (corresponding to the time-resolved measurement), the following relations hold.

$$J(\mu_s', \mu_a, t)=B_0 A(\mu_s', t)\exp(-\mu_a ct) \quad (3)$$

$$\ln[J(\mu_s', \mu_a, t)]=-\mu_a ct+\ln[B_0 A(\mu_s', t)] \quad (4)$$

$$(\partial/\partial\mu_a)J(\mu_s', \mu_a, t)=-ctB_0 A(\mu_s', t)\exp(-\mu_a ct) \quad (5)$$

$$(\partial/\partial\mu_a)\ln[J(\mu_s', \mu_a, t)]=-ct \quad (6)$$

Here, formula (3) is a rewritten form of formula (2).

Among the above four formulas, formula (3) or (4) is convenient, for example, for quantification of concentration of hemoglobin in a living tissue. Namely, the effect of scattering can be eliminated by performing measurement with light having two or more different wavelengths at which the scattering coefficients are equal or regarded as equal, then obtaining ln $J(\mu_s', \mu_a, t)$, and taking a ratio of values of ln J for the two wavelengths.

The inventor found out that because a quantity of detected light I is a time integration of the above $J(\mu_s', \mu_a, t)$, the following basic relations can be obtained as to the quantity of detected light I (a value of time integration, corresponding to CW measurement). A Laplace transform $(s=c\mu_a)$ of $A(\mu_s', t)$ will be represented hereinafter by $F[A(\mu_s', t)]$.

$$\begin{aligned} I(\mu_s', \mu_a) &= B_0 \int_0^\infty A(\mu_s', t)\exp(-\mu_a ct)dt \quad (7)\\ &= B_0 F[A(\mu_s', t)] \end{aligned}$$

$$\ln[I(\mu_s', \mu_a)] = \ln B_0 + \ln[F[A(\mu_s', t)]] \quad (8)$$
$$(\partial/\partial\mu_a)I(\mu_s', \mu_a) = -B_0 cF[tA(\mu_s', t)] \quad (9)$$

$$\begin{aligned}(\partial/\partial\mu_a)\ln[I(\mu_s', \mu_a)] &= -cF[tA(\mu_s', t)]/F[A(\mu_s', t)] \quad (10)\\ &= -c<t> = -<L(\mu_a)>\end{aligned}$$

$<L(\mu_a)>$ in above formula (10) is equal to weighted mean $c<t>$ of distribution of $J(\mu_s', \mu_a, t)$ in formula (3), which is called as a barycenter, average flight pathlength, or average optical pathlength.

This average flight pathlength $<L(\mu_a)>$ can be calculated by arithmetic processing of time-resolved re-emission (waveform) $J(\mu_s', \mu_a, t)$ of detection signal. It can also be calculated by another method, for example from a phase delay of photodetection signal to incidence of modulated light. Since this average flight pathlength $<L(\mu_a)>$ is a quantity obtainable by utilizing the whole of a photodetection signal, that is, a quantity in the integral form, high signal-to-noise ratios (S/N) can be achieved. Generally, the average flight pathlength $<L(\mu a)>$ is dependent on $\mu_a$.

The above is also verified by Monte Carlo simulation. The above description tells us that for utilizing photon diffusion equations, it is adequate to use a new diffusion constant D as defined by eliminating the absorption coefficient from the conventional diffusion constant. Namely, the new diffusion constant D is defined as follows.

$$D=1/(3\mu_s')=1/[3(1-g)\mu_s] \quad (11)$$

The inventor of the present application first discloses the above views. These results and deduction therefrom do not contradict with empirically obtained facts or views heretofore as far as the inventor of the present application knows.

Then, the present invention further develops the above view; for example, formula (10) is expanded as follows. First, the following formula is obtained from formula (10).

$$\ln I(\mu_a', \mu_a) = -\int_0^{\mu_a} <L(\mu_a)> d\mu_a + \ln B_0 + C_0 \quad (12)$$

$$= -G(\mu_a) + \ln B_0 + C_0$$

Here, $C_0$ is an integration constant, and $G(\mu_a)$ is defined as follows.

$$G(\mu_a) = \int_0^{\mu_a} <L(\mu_a)> d\mu_a \quad (13)$$

Supposing the scattering medium contains an absorptive constituent and $\epsilon_1$, $\epsilon_2$ represent absorption coefficients per unit concentration of the absorptive constituent for the respective light of wavelength $\lambda_1$ and $\lambda_2$, respectively, the concentration V of the absorptive constituent is given as follows.

$$V(\epsilon_1-\epsilon_2)=(\mu_{a1}-\mu_{a2}) \quad (14)$$

In the formula, $\mu_{a1}$ and $\mu_{a2}$ are the absorption coefficients of the absorptive constituent at wavelengths $\lambda_1$ and $\lambda_2$, respectively.

Thus, assuming that the average flight pathlengths, $<L_1(\lambda_1)>$ and $<L_1(\lambda_2)>$, and the light quantities, $I_1(\lambda_1)=I_1(\mu_{a1})$ and $I_1(\lambda_2)=I_1(\mu_{a2})$, are detected at a photodetection point $r_1$ for the incident light of the wavelength $\lambda_1$ (incident light intensity $B_1$) and the wavelength light of $\lambda_2$ (incident light intensity $B_2$), the following relation holds.

$$\ln \frac{I_1(\mu_{a1})}{I_1(\mu_{a2})} = G_1(\mu_{a2}) - G_1(\mu_{a1}) + \ln \frac{B_1}{B_2} \quad (15)$$

$$= \int_{\mu_{a1}}^{\mu_{a2}} L_1(\mu_a) d\mu_a + \ln \frac{B_1}{B_2}$$

Accordingly, there exists $\xi$ satisfying the following relation by the mean value theorem.

$$\ln[I_1(\lambda_1)/I_1(\lambda_2)]=(\mu_{a2}-\mu_{a1})L_1(\xi)+\ln[B_1/B_2] \quad (16)$$

Here, $\mu_{a1} \leq \xi \leq \mu_{a2}$ or $\mu_{a1} \geq \xi \geq \mu_{a2}$.

On the other hand, $L_1(\xi)$ can be expressed as follows using the average flight pathlengths, $<L_1(\lambda_1)>$ and $<L_1(\lambda_2)>$.

$$L_1(\xi)=p<L_1(\lambda_1)>+(1-p)<L_1(\lambda_2)> \quad (17)$$

Here, p is an appropriate value to satisfy the condition of $0 \leq p \leq 1$.

The inventor thus found out that if $B_1=B_2$ the concentration V of the absorptive constituent can be calculated according to the following formula.

$$V = (\epsilon_2-\epsilon_1)^{-1}[L_1(\xi)]^{-1} \times \ln[I_1(\lambda_1)/I_1(\lambda_2)] \quad (18)$$

$$= (\epsilon_2-\epsilon_1)^{-1} \times [p<L_1(\lambda_1)>+(1-p)<L_1(\lambda_2)>]^{-1} \times$$

$$\ln[I_1(\lambda_1)/I_1(\lambda_2)]$$

Here, because $\epsilon_2$ and $\epsilon_1$, are known quantities, the concentration V of a specific absorptive constituent can be calculated from the values obtained by measurement, that is, from the average flight pathlengths $<L_1(\lambda_1)>$ and $<L_1(\lambda_2)>$, the light quantities $\ln I_1(\lambda_1)$ and $\ln I_1(\lambda_2)$, and the value of p that can be empirically determined.

In actual measurement, sufficient measurement accuracy can be achieved using p=½ and an average value of $<L_1(\lambda_1)>$ and $<L_1(\lambda_2)>$ for $L(\xi)$ as follows.

$$L(\xi)=(\frac{1}{2})[<L_1(\lambda_1)>+<L_1(\lambda_2)>] \quad (19)$$

More generally, the inventor found out that if $B_1 \neq B_2$ and if photodetection is carried out at photodetection points $r_1$ and $r_2$ for the incident light of the wavelength $\lambda_1$ (incident light intensity $B_1$) and the wavelength $\lambda_2$ (incident light intensity $B_2$) to detect the average flight pathlengths $<L_1(\lambda_1)>$, $<L_1(\lambda_2)>$, $<L_2(\lambda_1)>$, $<L_2(\lambda_2)>$, and the light quantities $I_1(\lambda_1)$, $I_1(\lambda_2)$, $I_2(\lambda_1)$, $I_2(\lambda_2)$, the concentration V of the absorptive constituent can be calculated according to the following formula.

$$V = (\epsilon_2-\epsilon_1)^{-1}[L_1(\xi_1)-L_2(\xi_2)]^{-1} \times \quad (20)$$

$$\ln\{[I_1(\lambda_1)I_2(\lambda_2)]/[I_1(\lambda_2)I_2(\lambda_1)]\}$$

$$= (\epsilon_2-\epsilon_1)^{-1} \times [p<L_1(\lambda_1)>+(1-p)<L_1(\lambda_2)>-$$

$$q<L_2(\lambda_1)>-(1-q)<L_2(\lambda_2)>]^{-1} \times$$

$$\ln\{[I_1(\lambda_1)I_2(\lambda_2)]/[I_1(\lambda_2)I_2(\lambda_1)]\}$$

Here, p is an appropriate value to satisfy the condition of $0 \leq p \leq 1$ and q is an appropriate value to satisfy the condition of $0 \leq q \leq 1$.

Also in this case, similar to the above case, because $\epsilon_2$ and $\epsilon_1$ are known quantities, the concentration V of a specific absorptive constituent can be calculated from the values obtainable by measurement, that is, the average flight pathlengths $<L_1(\lambda_1)>$, $<L_1(\lambda_2)>$, $<L_2(\lambda_1)>$, $<L_2(\lambda_2)>$, the light quantities $\ln I_1(\lambda_1)$, $\ln I_1(\lambda_2)$, $\ln I_2(\lambda_1)$, $\ln I_2(\lambda_2)$, and the values of p and q that can be empirically determined.

Further, sufficient measurement accuracy can also be achieved in this case using the following.

$$L_1(\xi_1)-L_2(\xi_2)=(\frac{1}{2})[<L_1(\lambda_1)>+<L_1(\lambda_2)>-<L_2(\lambda_1)>-<L_2(\lambda_2)>] \quad (21)$$

If a scattering medium contains two absorptive constituents, measurement should be done with light including three wavelengths. Supposing concentrations of the two absorptive constituents are $V_1$, $V_2$, two simultaneous equations hold for $V_1$ and $V_2$, like formula (18) or (20). Accordingly, $V_1$ and $V_2$ can be obtained by solving the simultaneous equations. More generally, if a scattering medium contains m absorptive constituents, concentrations of the m absorptive constituents can be measured using light of (m+1) wavelengths.

Figure 3A:
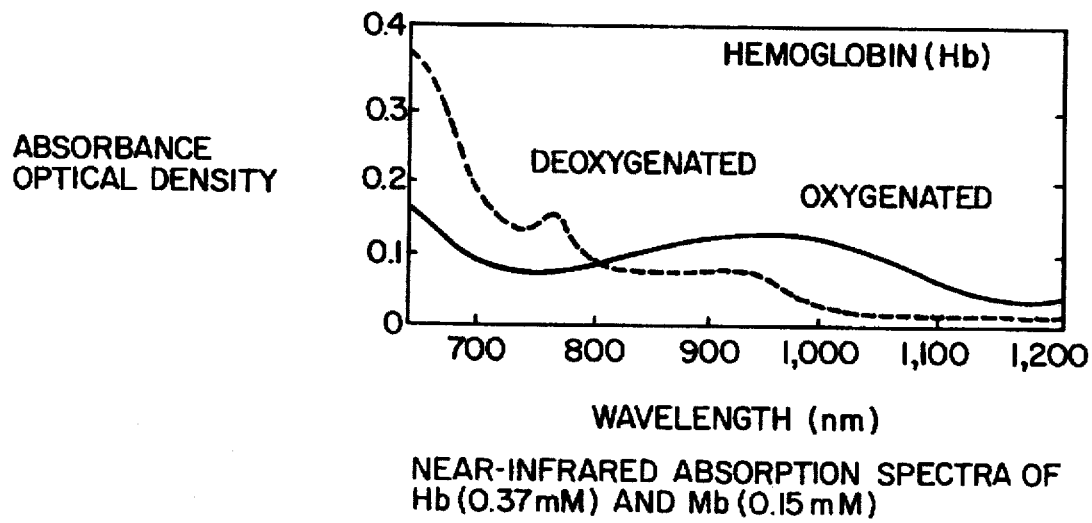
FIG. 3 is a graph to show absorption spectra of various biological materials.
Figure 3B:
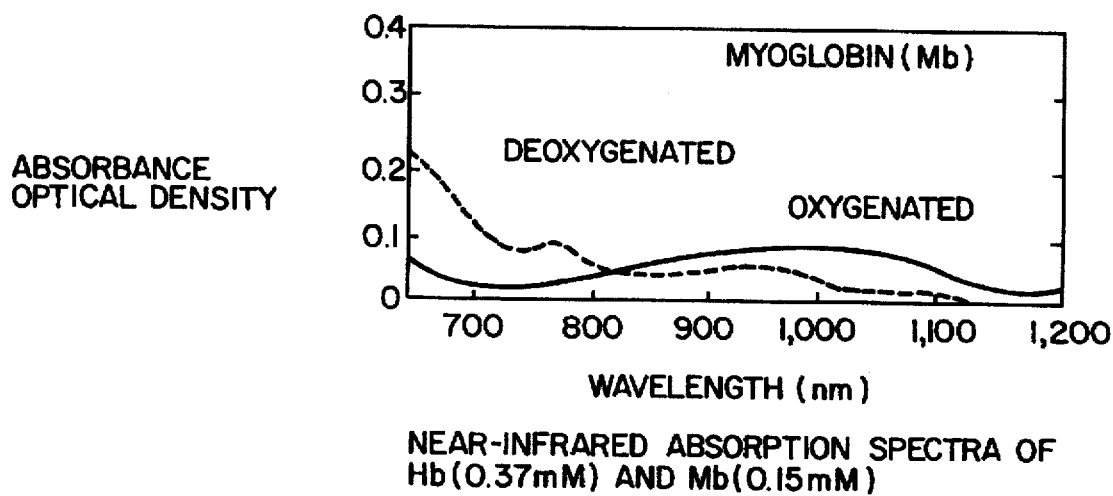

For example, FIG. 3 shows absorption spectra of oxygenated hemoglobin and deoxygenated hemoglobin and oxygenated myoglobin and deoxygenated myoglobin. It is important, for example, to measure a ratio of an oxygenated component and a deoxygenated component of hemoglobin in the brain. In this case, measurement according to the above-discussed principle can be applied utilizing light having different wavelengths to show a great difference in absorption coefficient between the oxygenated component and the deoxygenated component, namely using the light of wavelengths in the range of 700 nm to 1.2 μm.

In the above description, the scattering coefficients of scattering constituents for the respective light different wavelengths are equal to each other or are regarded as having a difference between them which is very small, if any. For actual living samples, the wavelengths can be selected so as to minimize the difference to the ignorable extent.

The above description clarified the method for measuring the concentration of a specific absorptive constituent for a variety of scattering media in different shapes. Now, embodiments of the present invention are explained below with reference to the accompanying drawings. In the following description with the drawings, same elements will be denoted by same reference numerals, and redundant description will be omitted.

(First Embodiment)

Figure 4:
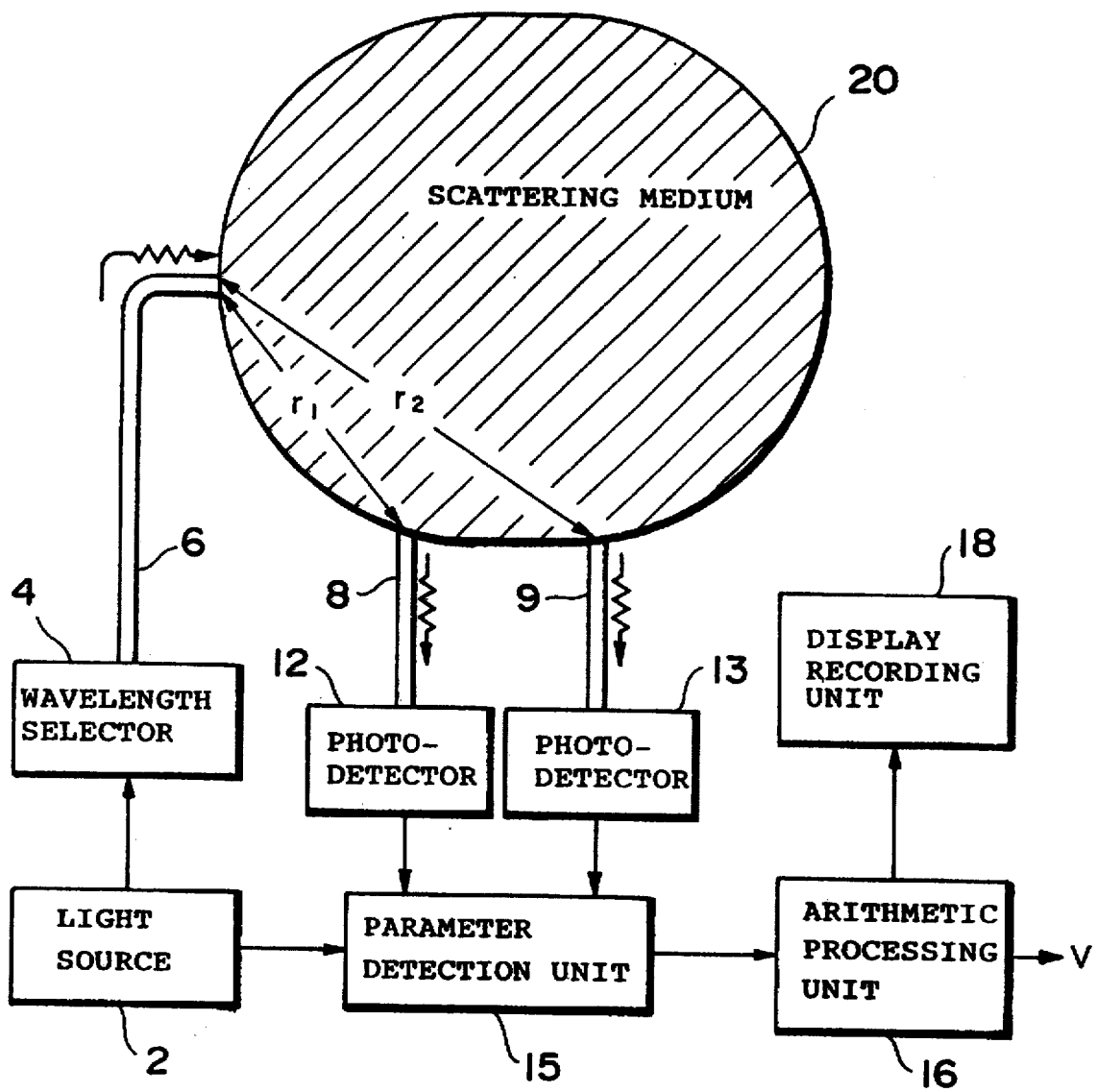
FIG. 4 is a structural drawing of an apparatus of the first embodiment.

FIG. 4 shows the first embodiment of the present invention and illustrates a method and apparatus arrangement for measuring a concentration of an absorptive constituent inside a scattering medium 20. This arrangement provides eight parameter values associated with light of two wavelengths ($\lambda_1$, $\lambda_2$) and two photodetection distances ($r_1$, $r_2$), and thus, the concentration of the absorptive constituent can be measured according to formula (20) discussed above.

A light source 2 is a laser diode, which emits pulsed light (pulsed light beams) of different wavelengths $\lambda_1$, and $\lambda_2$. The time width of the pulsed light can be freely selected normally in the range of about 10 ps to 100 ns as long as it is short enough to allow derivation of average flight pathlengths from a photodetection signal. Further, the wavelengths of light need to properly be selected depending upon an object to be measured. Generally, light of above 700 nm is often used for living samples because of absorption of hemoglobin and the like. The light source may be a light-emitting diode, a HeNe laser, etc. in addition to the laser diode.

The pulsed light beams from the light source 2 are subjected to wavelength selection in a wavelength selector 4, and either of the pulsed light beams of the selected wavelength is selectively guided through a light guide 6 to be made incident into the surface of the scattering medium 20, which is the measured object. In this case, another method for making pulsed light beams of two wavelengths simultaneously incident into the surface of the scattering medium may be employed, and in that case the wavelength selector 4 is omitted.

A space between the light guide 6 and the scattering medium 20 is kept fine enough in the embodiment of FIG. 4. In actual applications, this space, however, may be expanded and filled with a liquid material or a jelly material (hereinafter referred to as an interface material) having a refractive index and a scattering coefficient nearly equal to those of the scattering medium 20. Namely, such an arrangement will raise no problems because the light diffusively propagates in the interface material to enter the measured object. In the cases where surface reflection of the scattering medium is problematic, the effect of the surface reflection etc. can be reduced by properly selecting the interface material.

The light diffusively having propagated through the inside the scattering medium is received by light guides 8 and 9 placed at positions having distances $r_1$ and $r_2$, respectively, from the position of incidence of the light. The interface material may be used here as well from the same reason as above.

First photodetector 12 and second photodetector 13 convert the optical signals into electric signals, amplify them if necessary, and then output respective photodetection signals. The photodetectors 12 and 13 may be selected from photomultiplier tubes, phototubes, photodiodes, avalanche photodiodes, PIN photodiodes, etc. Any photodetector may be selected as long as it has spectral sensitivity characteristics for detecting the light of the predetermined wavelengths, and the necessary time response speed. If the optical signals are weak, high-gain photodetectors are to be used. Further, photons may be counted by the time correlation photon counting method. Portions of the photodetectors other than the light-receiving surfaces are preferably arranged to absorb or shield the light. In the cases where the pulsed light beams of two wavelengths are made simultaneously incident into the scattering medium as described previously, it is preferred that one appropriate wavelength selection filter (not shown) be interposed one between the photodetector 12 and the scattering medium 20 and the other between the photodetector 13 and the scattering medium 20.

A parameter detection unit 15 detects light quantities and average flight pathlengths from these photodetection signals. Since a light quantity is a time integration value of a photodetection signal, it can be readily obtained by integrating the photodetection signal. Since an average flight pathlength is a weighted mean of time-resolved re-emission (waveform) of a photodetection signal obtained for a short light-pulse incidence, it can be readily obtained by executing, for example, the arithmetic processing of formula (10) described previously, or arithmetic processing equivalent thereto from the time-resolved re-emission (waveform) of the photodetection signal. In this case, the parameter detection unit utilizes, with necessity, signals synchronized with generation of light pulses of the light source 2.

An arithmetic processing unit 16 calculates the concentration V of the absorptive constituent, based on the previous formula (20), using the eight parameter values obtained in the parameter detection unit, i.e., the light quantities $I_1(\lambda_1)$, $I_1(\lambda_2)$ and the average flight pathlengths $<L_1(\lambda_1)>$, $<L_1(\lambda_2)>$ at the position $r_1$ for incidence of the pulsed light of the wavelengths $\lambda_1$ and $\lambda_2$, and the light quantities $I_2(\lambda_1)$, $I_2(\lambda_2)$ and the average flight pathlengths $<L_2(\lambda_1)>$, $<L_2(\lambda_2)>$ at the position $r_2$ for incidence of the pulsed light of the wavelengths $\lambda_1$ and $\lambda_2$. On this occasion, the processing unit uses the constants p and q which can be empirically determined. In actual measurement, sufficient accuracy is achieved with p=q=½. The arithmetic processing is carried out at high speed, for example, by a microcomputer incorporated in the arithmetic processing unit.

If incident light intensities of the wavelengths $\lambda_1$ and $\lambda_2$ in the pulsed light into the scattering medium 20 are equal to each other, or can be controlled so as to become equal to each other or become a predetermined ratio previously known, the second photodetector 13 can be omitted. In this case, the parameter detection unit 15 obtains four parameters, the light quantities $I_1(\lambda_1)$, $I_1(\lambda_2)$ and the average flight pathlengths $<L_1(\lambda_1)>$ and $<L_1(\lambda_2)>$ at the position $r_1$ for incidence of the pulsed light of the wavelengths $\lambda_1$ and $\lambda_2$. Accordingly, the arithmetic processing unit 16 calculates the concentration V of the absorptive constituent, based on the above formula (18), using these parameter values. On this occasion, the processing unit uses the constant p that can be empirically determined, but in actual measurement, sufficient accuracy can be achieved with p=½. The arithmetic processing is executed at high speed, for example, by the microcomputer incorporated in the arithmetic processing unit.

The above description illustrated the method in which the light was made incident at a position and was was detected at two points different therefrom. It is, however, clear that in actual applications light beams of different wavelengths may be made incident at two positions and these light beams may be detected in parallel or in time division at another point or other points.

As described above, the above embodiment may employ either the method using the light including beams of different wavelengths made incident or the method using the light beams of different wavelengths made incident in time division. The former may employ a method arranged to make the light beams of different wavelengths in concentric beams and to wavelength-select the light beams by a wavelength selection filter provided immediately before the position of incidence of light, a method arranged to make the light beams incident into the scattering medium as they are and to wavelength-select the light beams by a wavelength selection filter provided immediately before the photodetector, or a method arranged to split each detected light into two beams, to wavelength-select each of the two beams, and to detect the beams using a total of four photodetectors in parallel. The latter may utilize a light beam switch using a mirror on the light source side, a wavelength switch using a filter, or a light switch using an optical switch.

Figure 5:
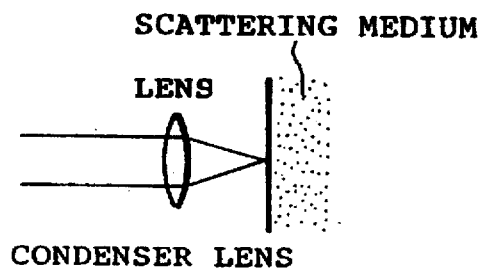
FIG. 5 to FIG. 8 are each explanatory drawings to show respective methods for guiding light into a scattering medium.
Figure 6:
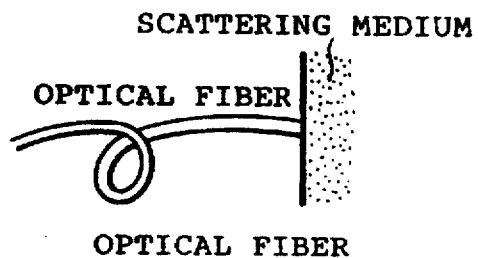
Figure 7:
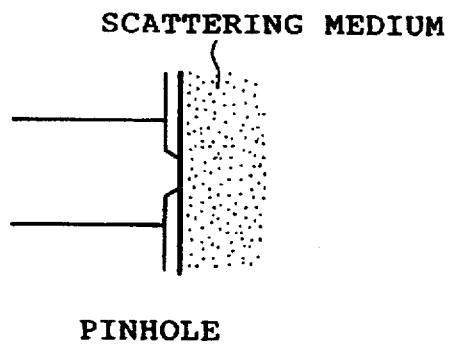
Figure 8:
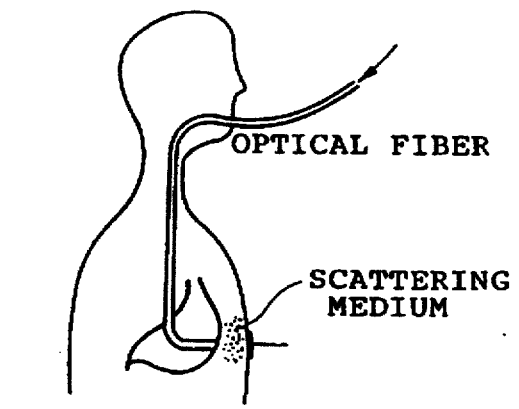

The means for guiding the light into the scattering medium may be a method using a condenser lens (FIG. 5), a method using an optical fiber (FIG. 6), a method utilizing a pinhole (FIG. 7), or a method for guiding the light into a body to apply it from inside, such as a gastrocamera (FIG. 8), in place of the optical guide shown in FIG. 4. Also, the light may be made incident in the form of a thick beam into the scattering medium. This case may be considered as a plurality of spot light sources arranged in the beam.

Figure 9:
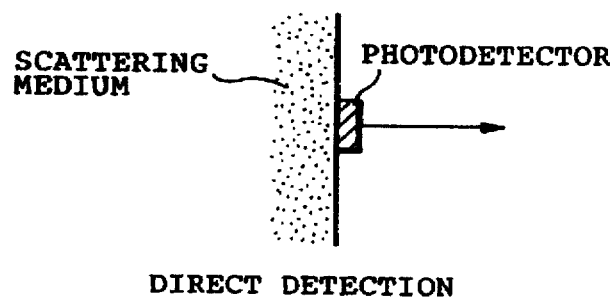
FIG. 9 to FIG. 11 are each explanatory drawings to show respective methods for receiving light.
Figure 10:
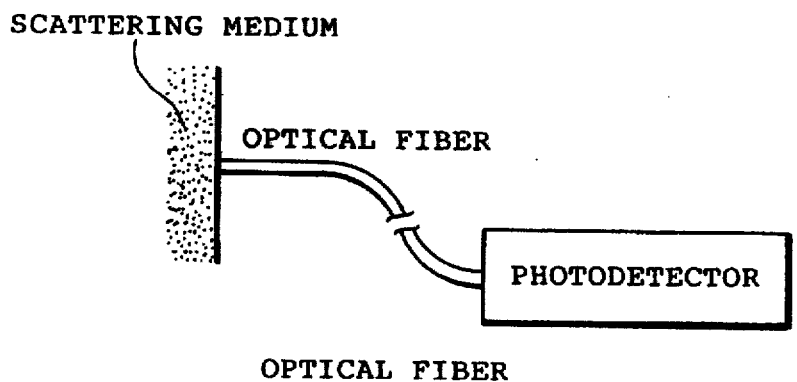
Figure 11:
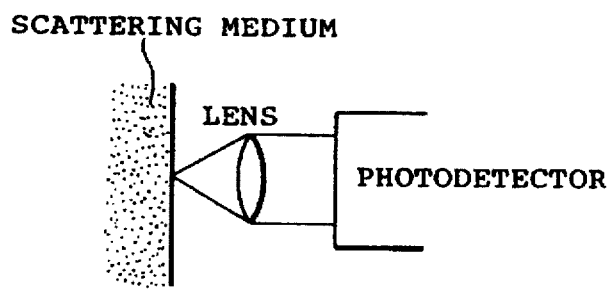

The means for detecting the light diffusively having propagated inside the scattering medium may be a method for directly detecting the light (FIG. 9), a method using an optical fiber (FIG. 10), or a method using a lens (FIG. 11), in addition to the method using the light guide shown in FIG. 4.

If the first embodiment as described above is arranged to use the light of three wavelengths, it can measure concentrations of two absorptive constituents in a scattering medium containing the two absorptive constituents, or a concentration of one absorptive constituent in a scattering medium containing a lot of absorptive constituents and a total concentration of the other absorptive constituents. For example, oxygenated hemoglobin and deoxygenated hemoglobin have different absorption coefficients depending upon the wavelengths, as shown in FIG. 3 in the previous description. Therefore, concentrations of those and oxygen saturation can be measured using the light of three wavelengths properly selected. Generally, concentrations of m absorptive constituents can be measured using light of (m+1) wavelengths. In addition, the measurement accuracy can be improved using light of wavelengths of more than (m+1).

If the above measurement is carried out at different times, a time change of concentration of absorptive constituent can be measured. Further, a spatial distribution of concentration can be measured by synchronous scanning (not shown) of the position of incidence of light and positions of photodetection with respect to the scattering medium and measuring concentrations of the absorptive constituent in respective portions of the scattering medium. The arithmetic processing unit 16 has a function to store concentration information of absorptive constituent thus obtained, and a display recording unit 18 displays or records the information.

The arithmetic processing can be executed at high speed by a computer device provided with a memory and a display.

(Second Embodiment)

Figure 12:
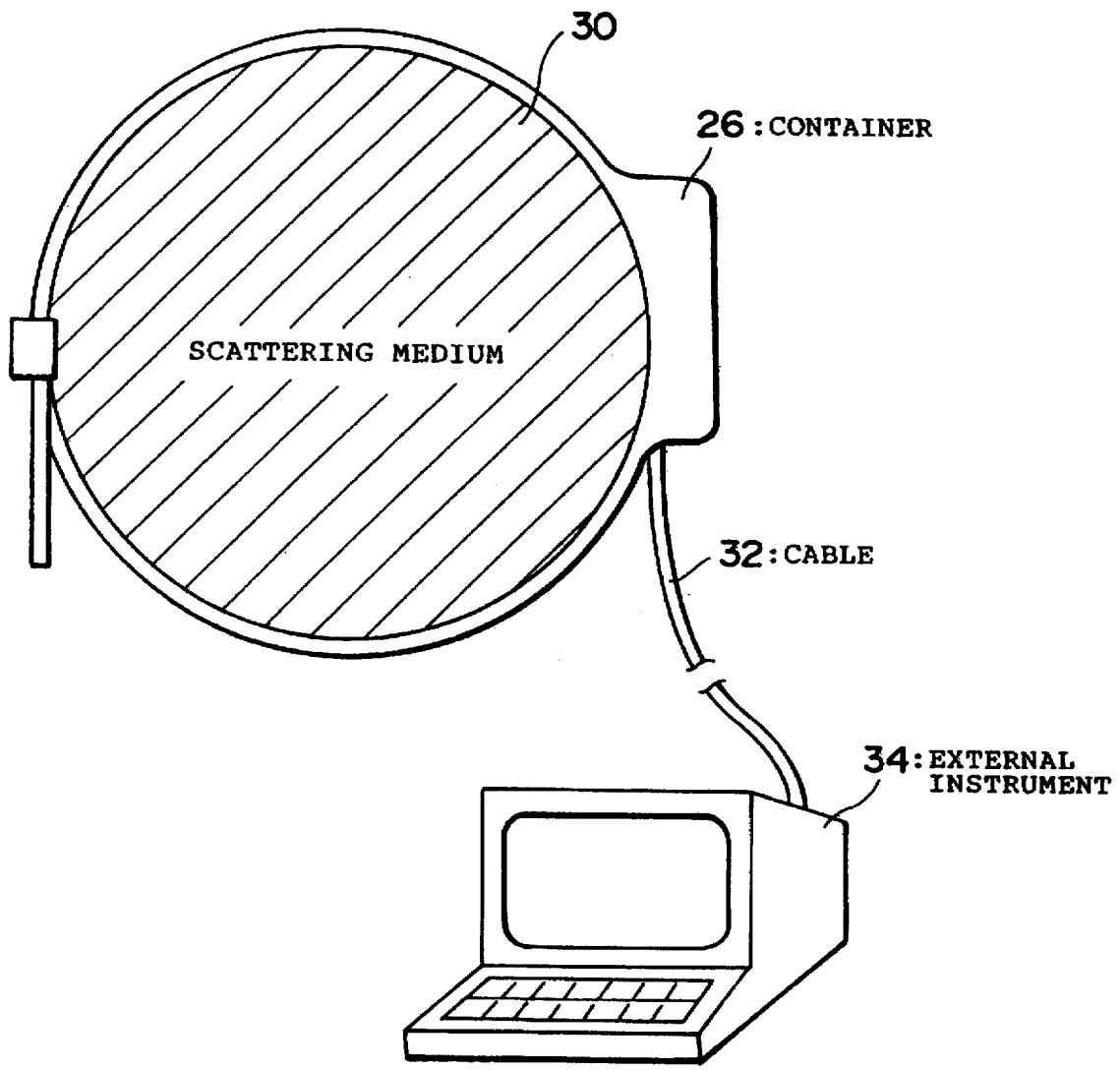
FIG. 12 is a structural drawing of an apparatus of the second embodiment.

FIG. 12 shows the second embodiment of the present invention to illustrate a method and apparatus arrangement for measuring or monitoring a concentration of oxygenated hemoglobin or oxygen saturation of hemoglobin (a ratio between a concentration of oxygenated hemoglobin to a concentration of overall hemoglobin) inside a scattering medium 30 such as a human head. This embodiment can measure the concentration of oxygenated hemoglobin and the oxygen saturation of hemoglobin by substituting twelve parameter values obtained using the light of three wavelengths ($\lambda_1$, $\lambda_2$, $\lambda_3$) and two photodetection distances ($r_1$, $r_2$) into three simultaneous equations based on formula (20) as discussed previously.

Figure 13:
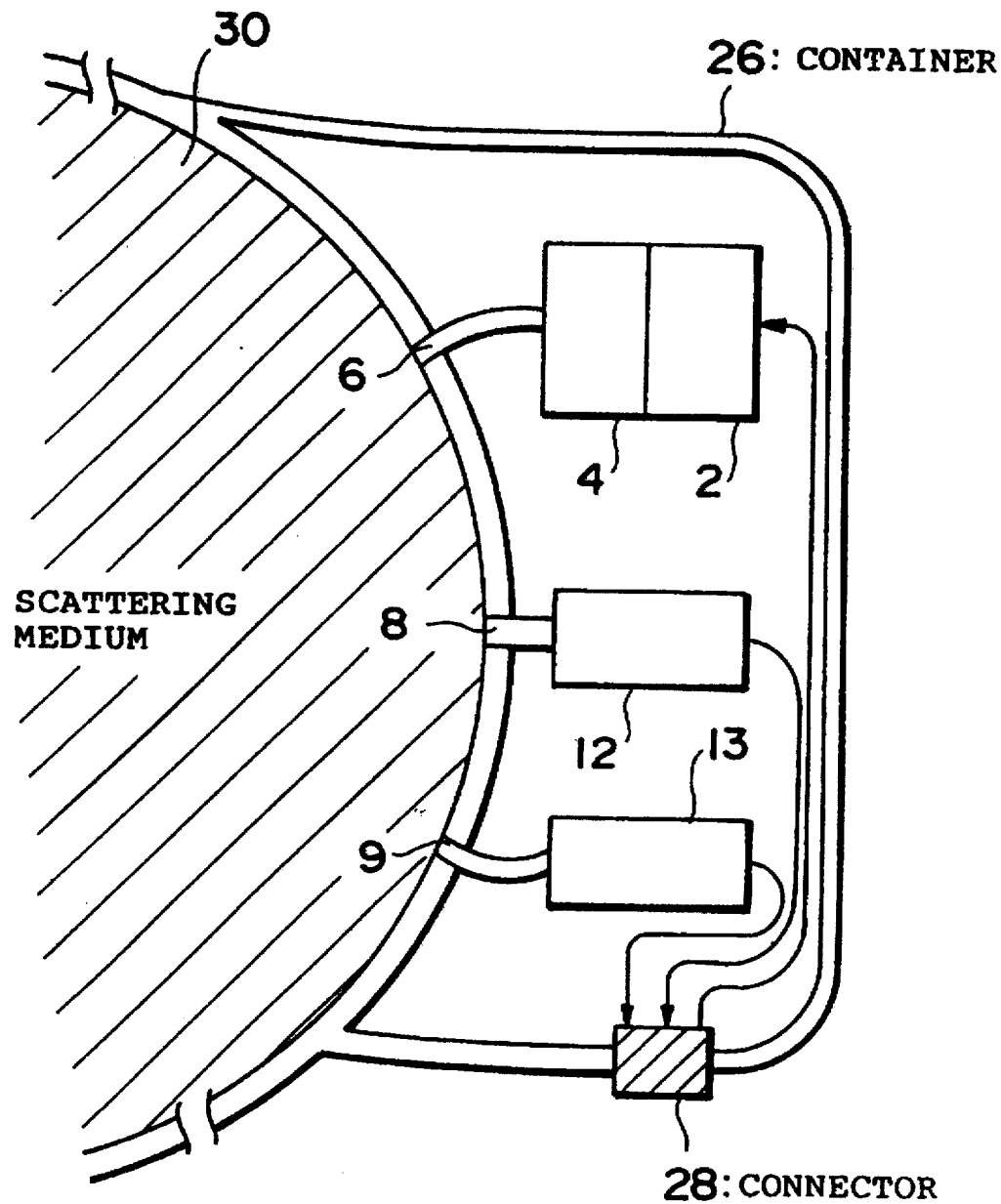
FIG. 13 is a structural drawing of light incidence and photodetection portions in the apparatus of the second embodiment.

A container 26 with a mount band is mounted on the head 30 like a headband. The apparatus shown in this embodiment uses the light of three predetermined wavelengths $\lambda_1$, $\lambda_2$, and $\lambda_3$, and the operation thereof is substantially the same as that of the apparatus of the first embodiment. FIG. 13 shows a part of the apparatus arrangement shown in FIG. 12, that is, the details of the inside of the container 26.

In FIG. 13, pulsed light (pulsed light beams) of the predetermined wavelengths $\lambda_1$, $\lambda_2$, and $\lambda_3$ emitted from the light source 2 are subjected to wavelength selection in the wavelength selector 4 and each light beam of the selected wavelength is selectively guided through the light guide 6 into the head 30. On this occasion, the three wavelengths are properly selected by reference to the absorption spectra of hemoglobin shown in previous FIG. 3.

The light diffusively having propagated through the inside of the head is received by the light guides 8 and 9 respectively placed at positions by distances $r_1$ and $r_2$, from the position of incidence of the light, and the first photodetector 12 and second photodetector 13 convert the light into electric signals and amplify the signals if necessary. The signals obtained herein are those for the three wavelengths and the two photodetection distances. The power supply and various signals are connected through a connector 28 attached to the container 26 to an external device 34 by a signal cable 32. A parameter detection unit (not shown) in the external device 34 obtains light quantities and average flight pathlengths for the three wavelengths and two photodetection distances, i.e. twelve parameters.

On this occasion, two simultaneous equations, similar to previous formula (20), hold for the signals obtained as to the wavelengths $\lambda_1$ and $\lambda_2$ and the signals obtained as to the wavelengths $\lambda_1$ and $\lambda_3$. Accordingly, similarly as in the first embodiment, the arithmetic processing unit (not shown) can calculate the concentration $V_1$ of oxygenated hemoglobin, the concentration $V_2$ of deoxygenated hemoglobin, and the oxygen saturation of hemoglobin $V_1/(V_1+V_2)$, and can also output or display them with necessity. This arithmetic processing is carried out at high speed, for example, by a computer built in the arithmetic processing unit. The above arrangement may be modified in such a manner that the signals are converted into electronic radio waves or optical signals in the container 26 and they are transferred to the external device 34 without interposition of the signal cable.

The above embodiment can utilize the light source, the light incidence portion, and the light detecting units as explained in the first embodiment. In case of human heads etc., there are some cases that the surface reflection or a gap between the light guide and the head causes a problem. The interface material as described previously can be effectively utilized for such cases. In such cases, the light guide shown in FIG. 13 is omitted, and an interface material having a scattering coefficient and an absorption coefficient nearly equal to those of the measured object is used between the head and the wavelength selector 4 and between the head and the photodetectors 12 and 13.

The above apparatus can be used not only in the measurement of inside the brain, but also in measurement or monitoring of the concentration of oxygenated hemoglobin in a leg muscle of a man in marathon, for example.

(Third Embodiment)

Figure 14:
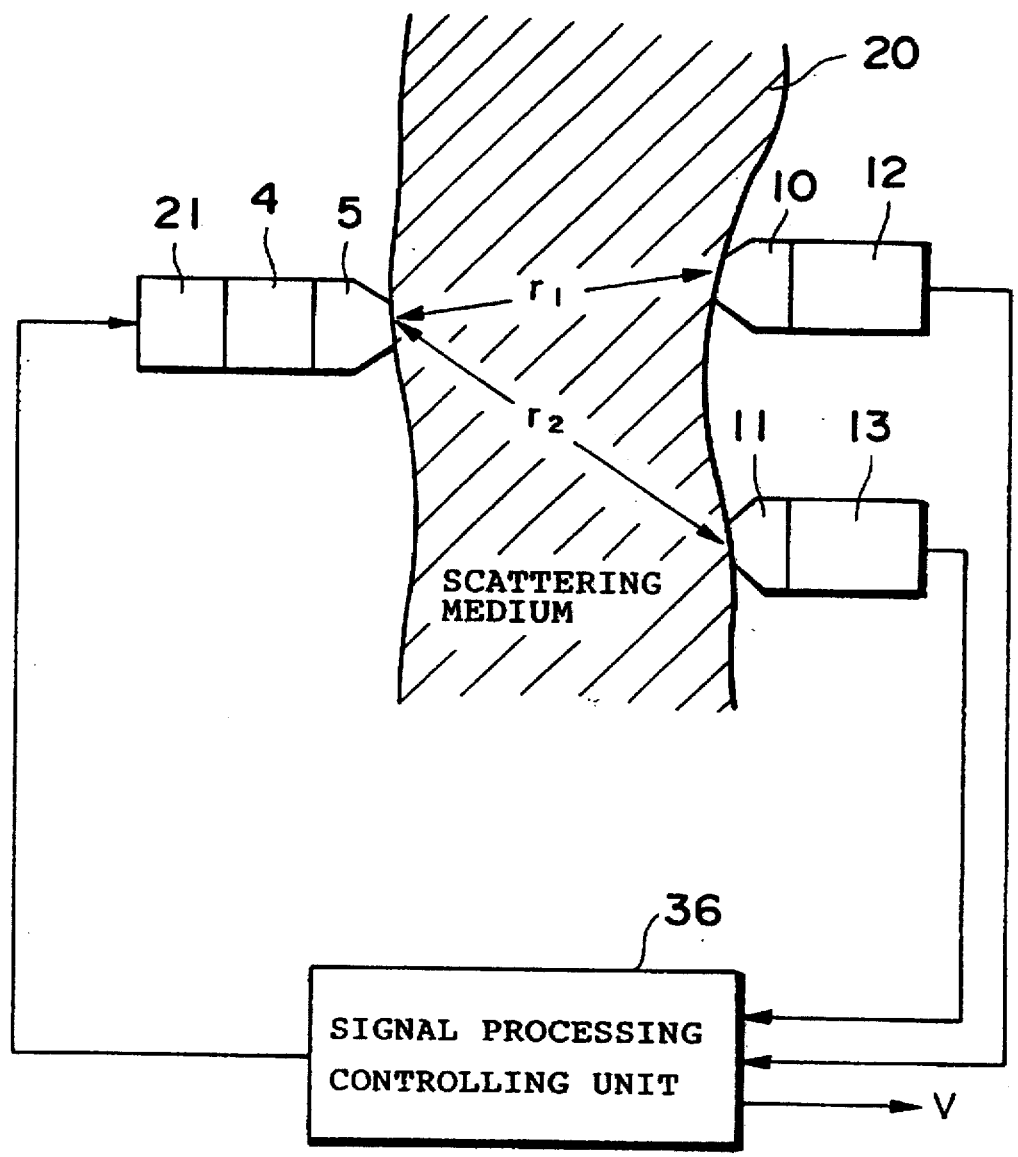
FIG. 14 is a structural drawing of an apparatus of the third embodiment.

FIG. 14 shows the third embodiment of the present invention, and illustrates a method and apparatus arrangement for measuring a concentration of an absorptive constituent inside a scattering medium 20, using sinusoidally modulated light. This embodiment utilizes a transmission type arrangement for measurement and measures the concentration of the absorptive constituent by making modulated light of two wavelengths ($\lambda_1$, $\lambda_2$) incident into the medium, detecting the light at positions of two photodetection distances ($r_1$ and $r_2$), and substituting parameter values obtained into formula (20) as discussed previously.

The sinusoidally modulated light of the wavelengths (or light wavelengths) $\lambda_1$ and $\lambda_2$ and a predetermined angular frequency (or a predetermined modulation angular frequency) $\omega$ generated by a modulation light source 21 is guided through the wavelength selector 4 to a light incidence portion 5 and then into the scattering medium 20. Here, the light incidence portion utilizes the previous method shown in FIG. 5, that is, the method using the lens, but may employ any other method.

Figure 15:
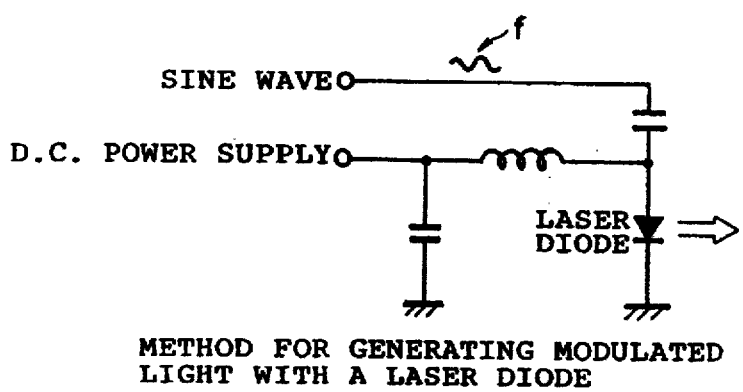
FIG. 15 is an explanatory drawing to show an example of a method for generating modulated light.
Figure 16:
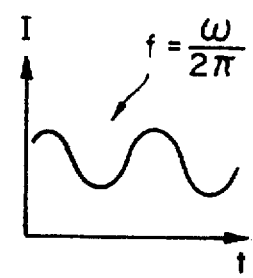
FIG. 16 is an explanatory drawing of the modulated light generated by the method shown in FIG. 15.
Figure 17:
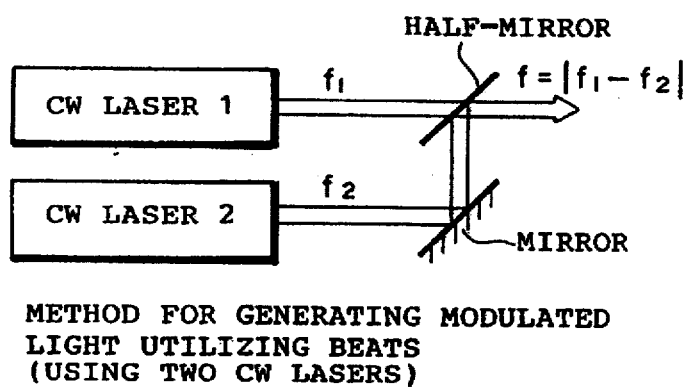
FIG. 17 is an explanatory drawing to show another example of the method for generating modulated light.
Figure 18:
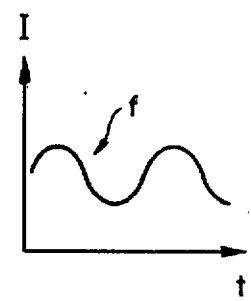
FIG. 18 is an explanatory drawing of the modulated light generated by the method shown in FIG. 17.
Figure 19:
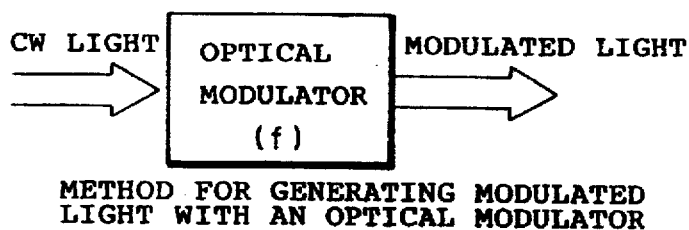
FIG. 19 is an explanatory drawing to show still another example of the method for generating modulated light.
Figure 20:
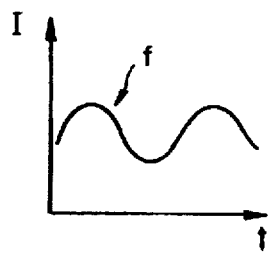
FIG. 20 is an explanatory drawing of the modulated light generated by the method shown in FIG. 19.

The sinusoidally modulated light of the predetermined angular frequency is generated by current modulation of a laser diode, as shown in FIGS. 15 and 16. The sinusoidally modulated light can also be generated by utilizing beats of two CW lasers as shown in FIGS. 17 and 18 or utilizing an optical modulator as shown in FIGS. 19 and 20.

The sinusoidally modulated light incident through the light incidence portion 5 into the scattering medium 20 diffusively propagates through inside the scattering medium, and part thereof enters first light-receiving portion 10 and second light-receiving portion 11. Here, the light-receiving portions employ, for example, the previous method shown in FIG. 11. The light entering the light-receiving portions 10 and 11 is converted each into electric signals by the photodetectors 12 and 13, respectively, and the electric signals are amplified as necessary. In this case, the distances are $r_1$ and $r_2$ between the light incidence point and the light-receiving points.

A signal processing controlling unit 36 performs control of the light source and arithmetic processing of the photodetection signals, outputs the concentration V of the absorptive constituent inside the scattering medium 20, and displays or records it as necessary.

Figure 21:
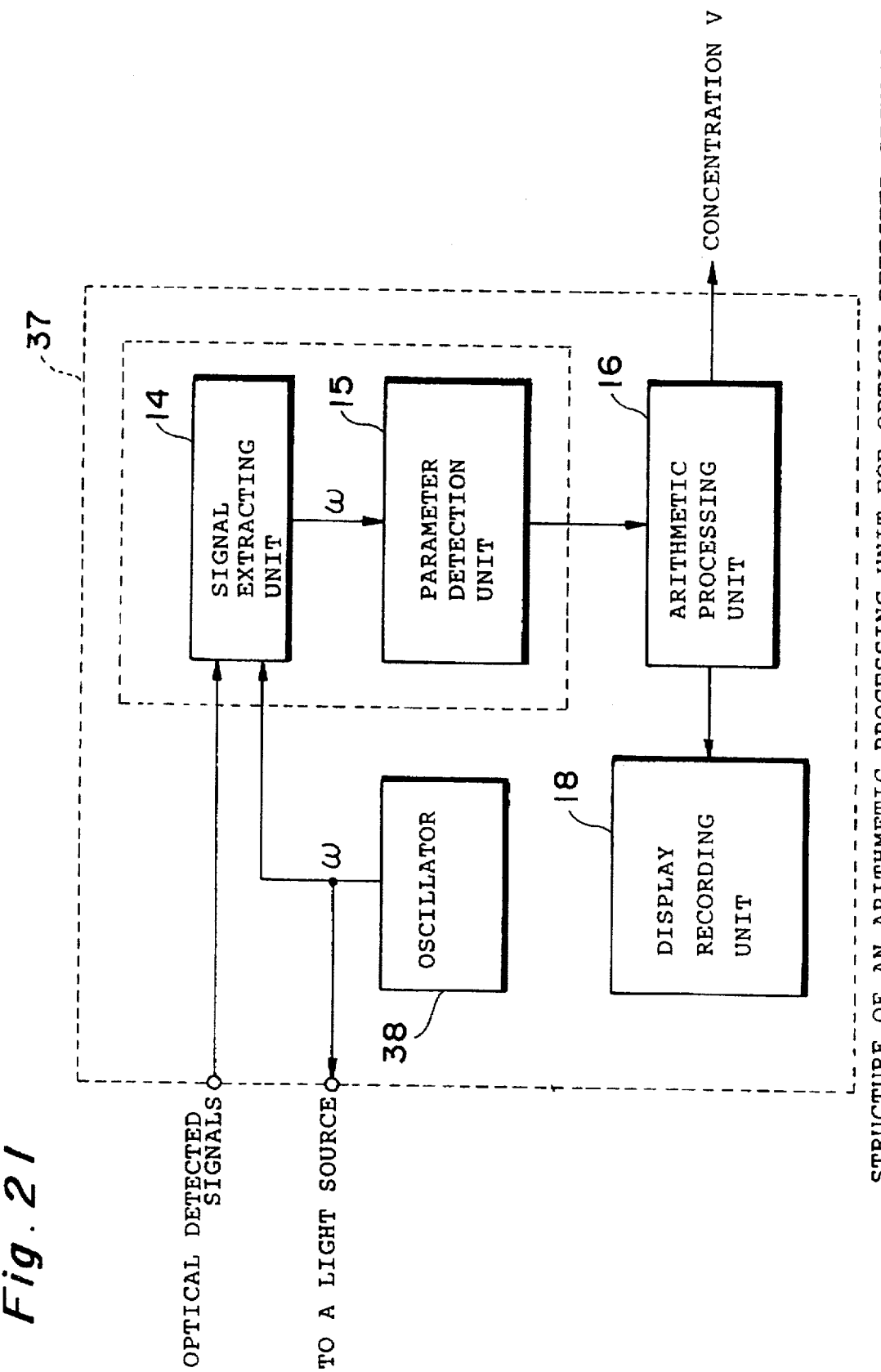
FIG. 21 is a structural drawing of an arithmetic processing unit for photodetection signals.

FIG. 21 shows a specific structural example of the portion for executing the arithmetic processing for the photodetection signals. The photodetection signals from the photodetectors 12 and 13 are led to a signal extracting unit 14, which extracts only signals with an angular frequency component of the predetermined value $\omega$ out of the respective photodetection signals. The signals with the predetermined angular frequency $\omega$ are photon density waves of the predetermined angular frequency $\omega$ diffusively having propagated through inside the scattering medium 20. Then a parameter detecting unit 15 detects amplitudes M and phase delays $\Phi$ of the signals of the predetermined angular frequency $\omega$.

The behavior of the modulated light inside the scattering medium as described above can be expressed by the Fourier transforms of formula (3) to formula (10). On this occasion, a ratio of the amplitudes of the signals of the above predetermined angular frequency (modulation angular frequency) $\omega$ detected at detection distance $r_1$ for the predetermined wavelengths (light wavelengths) $\lambda_1$ and $\lambda_2$, i.e., $M_1(\lambda_1)/M_1(\lambda_2)$, is expressed as follows using the light quantities $I_1(\lambda_1)$ and $I_1(\lambda_2)$ used in previous formula (20).

$$M_1(\lambda_1)/M_1(\lambda_2) = I_1(\lambda_1)/I_1(\lambda_2) \quad (22)$$

Accordingly, the ratio of light quantities in formula (18) or formula (20) is equal to the above ratio of amplitudes.

When each frequency $\omega$ is sufficiently smaller than the product between the speed of light in the medium and the absorption coefficient thereof, that is, when $\omega \ll c\mu_a$, the phase delay $\Phi$ is proportional to the average flight pathlength $\langle L(\mu_a) \rangle$ described previously.

For example, the phase delay $\Phi$ for the transmission type measurement shown in FIG. 14 is given by the following.

$$\Phi(r, \omega) = \omega c^{-1} \langle L(\mu_a) \rangle$$

Accordingly, the average flight pathlength $\langle L(\mu_a) \rangle$ can be easily obtained from the known values, $\omega$ and c, and the measured value $\Phi$. Such a relation also holds for half-space reflection-type measurement. In the case that the modulation frequency is high, the above mentioned relation should be modified.

As discussed above, the measured parameters necessary for calculating the concentration V of the absorptive constituent using previous formula (18) or formula (20), i.e., light quantity ratios $I_1(\lambda_1)/I_1(\lambda_2)$, $I_2(\lambda_1)/I_2(\lambda_2)$ and the average flight pathlengths $\langle L_1(\lambda_1) \rangle$ and $\langle L_1(\lambda_2) \rangle$, $\langle L_2(\lambda_1) \rangle$ and $\langle L_2(\lambda_2) \rangle$ at the photodetection distances $r_1$ and $r_2$ for the incident light of the wavelengths $\lambda_1$ and $\lambda_2$ are provided. On this occasion, the constants p and q that can be empirically determined are used similarly as in the first embodiment, but in actual measurement sufficient accuracy can be achieved with $p = q = \frac{1}{2}$.

The arithmetic processing unit 16 uses the parameters obtained above to execute the processing expressed by previous formula (18) or formula (20) to output the concentration V of the absorptive constituent. The concentration value is displayed or recorded with necessity. The above processing is normally executed at high speed by a computer device provided with a memory and a display.

A commercially available lock-in amplifier may be used as the signal extracting unit 14 and parameter detection unit 15. The lock-in amplifier can extract a signal of the predetermined frequency component (modulation frequency component) $\omega$ from a photodetection signal and can detect an amplitude M and a phase delay $\Phi$ of the signal. On this occasion, it utilizes a signal of angular frequency $\omega$ synchronized with the modulated light, as a reference signal.

In the above case, dc components $m_{dc}$ of the photodetection signals from the photodetectors 12 and 13 are values at $\omega = 0$, which correspond to light quantities I of formula (18) or formula (20). Such dc components $m_{dc}$ can be easily extracted using a low-pass filter. Accordingly, the above third embodiment may use the dc components $m_{dc}$ detected at the positions of detection distances $r_1$ and $r_2$ for the predetermined wavelengths, instead of the amplitudes of the signals of the predetermined angular frequency $\omega$.

Further, if the above measurement is carried out at different times, a time change of concentration of absorptive constituent can be measured, naturally. Further, if the position of incidence of light and the positions of detection of light are relatively scanned in synchronization with respect to the scattering medium 20 (not shown) in the above arrangement, a spatial distribution of concentration of absorptive constituent can be measured. On this occasion, a photodetection system having plural channels can be utilized.

If the third embodiment as described above is modified to use the light of three wavelengths, it can measure concentrations of two absorptive constituents in a scattering medium containing the two absorptive constituents, or a concentration of one absorptive constituent in a scattering medium containing a lot of absorptive constituents and a total concentration of the other absorptive constituents. More generally, concentrations of m absorptive constituents can be measured using light of (m+1) wavelengths. In addition, the measurement accuracy can be improved using light of wavelengths of more than (m+1).

The above processing is normally carried out at high speed by a computer provided with a memory and a display.

(Fourth Embodiment)

The present embodiment is achieved by modifying the third embodiment in such a manner that the sinusoidally modulated light of the predetermined frequency and the wavelengths $\lambda_1$ and $\lambda_2$ generated by the light source in the third embodiment is replaced by modulated light of predetermined repetition frequency (modulation frequency) in an arbitrary waveform. Namely, the third embodiment used the sinusoidally modulated light of the predetermined angular frequency, but the technique of the third embodiment can be applied without change to a specific frequency component included in any waveform of the modulated light as long as it contains the predetermined frequency component. For example, repetitive pulsed light includes frequency components of the repetition frequency and integral multiples thereof, and thus, the technique of the third embodiment can be applied as it is to either one of the frequency components. Required performance of the modulated light of the predetermined repetition frequency is stable repetition frequency and stable light intensity.

As described above, the method and apparatus for measuring the concentration of the absorptive constituent inside the scattering medium according to the present invention permits absolute-value measurement of the concentration of the absorptive constituent inside the scattering medium having any exterior shape consisting of faces not permitting reentrant (reentry) of light. Further, the invention permits measurement of the time change or spatial distribution of concentration. Further, because the measuring apparatus to which the present invention is applied uses the measured parameters in the form of time integration of light signals, the utility factor of light is enhanced and the signal-to-noise ratio is increased, thus achieving high measurement accuracy. Accordingly, the present invention permits real-time measurement of an amount of oxygen in the brain, an amount of oxygen in a leg muscle of a man while exercising, and a concentration of an absorptive constituent in a living tree etc.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 228253/1994 filed on Sep. 22, 1994 is hereby incorporated by reference.

What is claimed is:

1. A method for measuring a concentration of an absorptive constituent in a scattering medium, comprising:

(a) a step of emitting light having two or more predetermined wavelengths at which scattering coefficients are equal or regarded as equal, toward a scattering medium which is a measured object;

(b) a step of making said light incident at a light incidence position into said scattering medium and letting said light propagate through said scattering medium;

(c) a step of detecting said light having propagated through said scattering medium, at one or more photodetection points different from said light incidence position, thereby acquiring one or more photodetection signals;

(d) a step of calculating light quantities and average flight pathlengths at said one or more photodetection points for said respective wavelengths of light, based on said one or more photodetection signals; and (e) a step of obtaining said concentration of said absorptive constituent by arithmetic processing using said light quantities and said average flight pathlengths, based on a predetermined relationship among said light quantities, said average flight pathlengths, and a difference between absorption coefficients per unit concentration of said absorptive constituent, for said respective wavelengths of light;

wherein said predetermined relationship among said light quantities, said average flight pathlengths, and said difference between the absorption coefficients per unit concentration of said absorptive constituent, for said respective wavelengths of light, is a relationship derived from a partial differentiation of a natural logarithm of a light quantity detected with respect to an absorption coefficient, which is equal to an average flight pathlength.

2. The method according to claim 1, wherein said light having two or more predetermined wavelengths is pulsed light.

3. The method according to claim 1, wherein said light having two or more predetermined wavelengths is sinusoidally modulated light having a predetermined modulation frequency component, wherein said light quantities are calculated from amplitudes of said predetermined modulation frequency component included in said photodetection signals, and wherein said average flight pathlengths are calculated from phase delays of said predetermined modulation frequency component.

4. The method according to claim 1, wherein said light having two or more predetermined wavelengths is sinusoidally modulated light having a predetermined modulation frequency component, wherein said light quantities are calculated from dc components of said photodetection signals, and wherein said average flight pathlengths are calculated from phase delays of said predetermined modulation frequency component included in said photodetection signals.

5. The method according to claim 1, wherein said light having two or more predetermined wavelengths is modulated light having a predetermined repetitive modulation frequency component, wherein said light quantities are calculated from amplitudes of one of said predetermined repetitive modulation frequency component and a frequency component of an integral multiple of said predetermined repetitive modulation frequency component included in said photodetection signals, and wherein said average flight pathlengths are calculated from phase delays of one of said predetermined repetitive modulation frequency component and the frequency component of the integral multiple of said predetermined repetition modulation frequency component.

6. The method according to claim 1, wherein said light having two or more predetermined wavelengths is modulated light having a predetermined repetitive modulation frequency component, wherein said light quantities are calculated from dc components of said photodetection signals, and wherein said average flight pathlengths are calculated from phase delays of one of said predetermined repetitive modulation frequency component and a frequency component of an integral multiple of said predetermined modulation frequency component included in said photodetection signals.

7. The method according to claim 1, wherein said step (e) comprises obtaining the concentration of the absorptive constituent in said scattering medium by arithmetic processing using said light quantities and said average flight pathlengths, based on a relationship expressed by the following formula:

$$V=(\epsilon_2-\epsilon_1)^{-1}\times[p<L_1(\lambda_1)>+(1-p)<L_1(\lambda_2)>]^{-1}\times\ln[I_1(\lambda_1)/I_1(\lambda_2)]$$

where

V: the concentration of the absorptive constituent, $\epsilon_1$: the absorption coefficient per unit concentration of the absorptive constituent for the light of the wavelength $\lambda_1$, $\epsilon_2$: the absorption coefficient per unit concentration of the absorptive constituent for the light of the wavelength $\lambda_2$, $<L_1(\lambda_1)>$: the average flight pathlength for the light of the wavelength $\lambda_1$ at a photodetection point $r_1$, $<L_1(\lambda_2)>$: the average flight pathlength for the light of the wavelength $\lambda_2$ at the photodetection point $r_1$, $I_1(\lambda_1)$: the quantity of detected light for the light of the wavelength $\lambda_1$ at the photodetection point $r_1$, $I_1(\lambda_2)$: the quantity of detected light for the light of the wavelength $\lambda_2$ at the photodetection point $r_1$, and p: a predetermined value satisfying 0<p<1.

8. The method according to claim 1, wherein said step (e) comprises obtaining the concentration of the absorptive constituent in said scattering medium by arithmetic processing using said light quantities and said average flight pathlengths, based on a relationship expressed by the following formula:

$$V = (\epsilon_2-\epsilon_1)^{-1}\times[p<L_1(\lambda_1)>+(1-p)<L_1(\lambda_2)>-$$
$$q<L_2(\lambda_1)>-(1-q)<L_2(\lambda_2)>]^{-1}\times$$
$$\ln\{[I_1(\lambda_1)\cdot I_2(\lambda_2)]/[I_1(\lambda_2)\cdot I_2(\lambda_1)]\}$$

where

V: the concentration of the absorptive constituent, $\epsilon_1$: the absorption coefficient per unit concentration of the absorptive constituent for the light of the wavelength $\lambda_1$, $\epsilon_2$: the absorption coefficient per unit concentration of the absorptive constituent for the light of the wavelength $\lambda_2$, $<L_1(\lambda_1)>$: the average flight pathlength at a photodetection point $r_1$ for the light of the wavelength $\lambda_1$, $<L_1(\lambda_2)>$: the average flight pathlength at the photodetection point $r_1$ for the light of the wavelength $\lambda_2$, $<L_2(\lambda_1)>$: the average flight pathlength at a photodetection point $r_2$ for the light of the wavelength $\lambda_1$, $<L_2(\lambda_2)>$: the average flight pathlength at the photodetection point $r_2$ for the light of the wavelength $\lambda_2$, $I_1(\lambda_1)$: the quantity of detected light at the photodetection point $r_1$ for the light of an intensity $B_1$ and the wavelength $\lambda_1$, $I_1(\lambda_2)$: the quantity of detected light at the photodetection point $r_1$ for the light of an intensity $B_2$ and the wavelength $\lambda_2$, $I_2(\lambda_1)$: the quantity of detected light at the photodetection point $r_2$ for the light of the intensity $B_1$ and the wavelength $\lambda_1$, $I_2(\lambda_2)$: the quantity of detected light at the photodetection point $r_2$ for the light of the intensity $B_2$ and the wavelength $\lambda_2$.

p: a predetermined value satisfying $0\leq p\leq 1$, and q: a predetermined value satisfying $0\leq q\leq 1$.

9. An apparatus for measuring a concentration of an absorptive constituent in a scattering medium, comprising:

(a) a light source for emitting light having two or more predetermined wavelengths at which scattering coefficients are equal or regarded as equal, toward a scattering medium which is a measured object;

(b) light incidence means for making said light incident at a light incidence position into said scattering medium and making said light propagate through said scattering medium;

(c) photodetection means for detecting said light having propagated through said scattering medium, at one or more photodetection points different from said light incidence position to acquire one or more photodetection signals;

(d) parameters calculation means for computing light quantities and average flight pathlengths at said one or more photodetection points for said respective wavelengths of light, based on said one or more photodetection signals; and (e) arithmetic processing means for obtaining said concentration of said absorptive constituent by arithmetic processing using said light quantities and said average flight pathlengths, based on a predetermined relationship among said light quantities, said average flight pathlengths, and a difference between absorption coefficients per unit concentration of said absorptive constituent, for said respective wavelengths of light;

wherein said predetermined relationship among said light quantities, said average flight pathlengths, and said difference between the absorption coefficients per unit concentration of said absorptive constituent, for said respective wavelengths of light, is a relationship derived from a partial differentiation of a natural logarithm of a light quantity detected with respect to an absorption coefficient, which is equal to an average flight pathlength.

10. The apparatus according to claim 9, wherein said light having two or more predetermined wavelengths is pulsed light.

11. The apparatus according to claim 9, wherein said light having two or more predetermined wavelengths is sinusoidally modulated light having a predetermined modulation frequency component, wherein said light quantities are calculated from amplitudes of said predetermined modulation frequency component included in said photodetection signals, and wherein said average flight pathlengths are calculated from phase delays of said predetermined modulation frequency component.

12. The apparatus according to claim 9, wherein said light having two or more predetermined wavelengths is sinusoidally modulated light having a predetermined modulation frequency component, wherein said light quantities are calculated from dc components of said photodetection signals, and wherein said average flight pathlengths are calculated from phase delays of said predetermined modulation frequency component included in said photodetection signals.

13. The apparatus according to claim 9, wherein said light having two or more predetermined wavelengths is modulated light having a predetermined repetitive modulation frequency component, wherein said light quantities are calculated from amplitudes of one of said predetermined repetitive modulation frequency component and a frequency component of an integral multiple of said predetermined repetitive modulation frequency component included in said photodetection signals, and wherein said average flight pathlengths are calculated from phase delays of one of said predetermined repetitive modulation frequency component and the frequency component of the integral multiple of said predetermined repetition modulation frequency component.

14. The apparatus according to claim 9, wherein said light having two or more predetermined wavelengths is modulated light having a predetermined repetitive modulation frequency component, wherein said light quantities are calculated from dc components of said photodetection signals, and wherein said average flight pathlengths are calculated from phase delays of one of said predetermined repetitive modulation frequency component and a frequency component of an integral multiple of said predetermined modulation frequency component included in said photodetection signals.

15. The apparatus according to claim 9, wherein said arithmetic processing means (e) obtains the concentration of the absorptive constituent in said scattering medium by arithmetic processing using said light quantities and said average flight pathlengths, based on a relationship expressed by the following formula:

$$V = (\epsilon_2 - \epsilon_1)^{-1}[p\langle L_1(\lambda_1)\rangle + (1-p)\langle L_1(\lambda_2)\rangle]^{-1} \times \ln[I_1(\lambda_1)/I_1(\lambda_2)]$$

where

V: the concentration of the absorptive constituent, $\epsilon_1$: the absorption coefficient per unit concentration of the absorptive constituent for the light of the wavelength $\lambda_1$, $\epsilon_2$: the absorption coefficient per unit concentration of the absorptive constituent for the light of the wavelength $\lambda_2$, $\langle L_1(\lambda_1)\rangle$: the average flight pathlength for the light of the wavelength $\lambda_1$ at a photodetection point $r_1$, $\langle L_1(\lambda_2)\rangle$: the average flight pathlength for the light of the wavelength $\lambda_2$ at the photodetection point $r_1$, $I_1(\lambda_1)$: the quantity of detected light for the light of the wavelength $\lambda_1$ at the photodetection point $r_1$, $I_1(\lambda_2)$: the quantity of detected light for the light of the wavelength $\lambda_2$ at the photodetection point $r_1$, and p: a predetermined value satisfying $0 \leq p \leq 1$.

16. The apparatus according to claim 9, wherein said arithmetic processing means (e) obtains the concentration of the absorptive constituent in said scattering medium by arithmetic processing using said light quantities and said average flight pathlengths, based on a relationship expressed by the following formula:

$$V = (\epsilon_2 - \epsilon_1)^{-1} \times [p\langle L_1(\lambda_1)\rangle + (1-p)\langle L_1(\lambda_2)\rangle - q\langle L_2(\lambda_1)\rangle - (1-q)\langle L_2(\lambda_2)\rangle]^{-1} \times$$
$$\ln\{[I_1(\lambda_1) \cdot I_2(\lambda_2)]/[I_1(\lambda_2) \cdot I_2(\lambda_1)]\}$$

where

V: the concentration of the absorptive constituent, $\epsilon_1$: the absorption coefficient per unit concentration of the absorptive constituent for the light of the wavelength $\lambda_1$, $\epsilon_2$: the absorption coefficient per unit concentration of the absorptive constituent for the light of the wavelength $\lambda_2$, $\langle L_1(\lambda_1)\rangle$: the average flight pathlength at a photodetection point $r_1$ for the light of the wavelength $\lambda_1$, $\langle L_1(\lambda_2)\rangle$: the average flight pathlength at the photodetection point $r_1$ for the light of the wavelength $\lambda_2$, $\langle L_2(\lambda_1)\rangle$: the average flight pathlength at a photodetection point $r_2$ for the light of the wavelength $\lambda_2$, $\langle L_2(\lambda_2)\rangle$: the average flight pathlength at the photodetection point $r_2$ for the light of the wavelength $\lambda_1$, $I_1(\lambda_1)$: the quantity of detected light at the photodetection point $r_1$ for the light of an intensity $B_1$ and the wavelength $\lambda_1$, $I_1(\lambda_2)$: the quantity of detected light at the photodetection point $r_1$ for the light of an intensity $B_2$ and the wavelength $\lambda_2$, $I_2(\lambda_1)$: the quantity of detected light at the photodetection point $r_2$ for the light of the intensity $B_1$ and the wavelength $\lambda_1$, $I_2(\lambda_2)$: the quantity of detected light at the photodetection point $r_2$ for the light of the intensity $B_2$ and the wavelength $\lambda_2$, p: a predetermined value satisfying $0 \leq p \leq 1$, and q: a predetermined value satisfying $0 \leq q \leq 1$.

* * * * *